US012496406B2

(12) United States Patent
Laubach et al.

(10) Patent No.: US 12,496,406 B2
(45) Date of Patent: Dec. 16, 2025

(54) PHARMACEUTICAL SYRINGE PISTON

(71) Applicant: West Pharmaceutical Services, Inc., Exton, PA (US)

(72) Inventors: Jeffrey M. Laubach, Emmaus, PA (US); Jurgen Brinkhues, Aachen (DE); Heike Gruen, Aachen (DE); Joel Worman, Palm Harbor, FL (US); Xia Zhao, Malvern, PA (US); Jason Mattia, Downingtown, PA (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 18/601,989

(22) Filed: Mar. 11, 2024

(65) Prior Publication Data

US 2024/0207528 A1 Jun. 27, 2024

Related U.S. Application Data

(60) Division of application No. 17/828,046, filed on May 31, 2022, now Pat. No. 11,951,289, which is a division of application No. 16/354,675, filed on Mar. 15, 2019, now Pat. No. 11,369,742, which is a continuation of application No. 14/758,042, filed as application No. PCT/US2013/035381 on Apr. 5, 2013, now Pat. No. 10,258,744.

(51) Int. Cl.
*A61M 5/315* (2006.01)

(52) U.S. Cl.
CPC . *A61M 5/31513* (2013.01); *A61M 2205/0222* (2013.01)

(58) Field of Classification Search
CPC .................. A61M 5/31513; A61M 2205/0222
See application file for complete search history.

(56) References Cited

U.S. PATENT DOCUMENTS

| | | | |
|---|---|---|---|
| 453,093 | A | 5/1891 | Sullivan |
| 6,142,977 | A | 11/2000 | Kolberg et al. |
| 6,511,459 | B1 | 1/2003 | Fago |
| 7,547,297 | B2 | 6/2009 | Brinkhues |
| 10,258,744 | B2 | 4/2019 | Laubach et al. |
| 11,266,786 | B2 | 3/2022 | Dietl |
| 11,369,742 | B2 | 6/2022 | Laubach et al. |

(Continued)

FOREIGN PATENT DOCUMENTS

| | | | |
|---|---|---|---|
| EP | 0148426 | A2 | 7/1985 |
| EP | 1674121 | A1 | 6/2006 |

(Continued)

OTHER PUBLICATIONS

Int'l Search Report issued Apr. 9, 2013 in Int'l Application No. PCT/US2013/035381.

(Continued)

*Primary Examiner* — Moshe Wilensky
(74) *Attorney, Agent, or Firm* — Blank Rome LLP

(57) ABSTRACT

A method for manufacturing a syringe is described. The syringe includes a barrel having an open proximal end, a piston shaft having proximal and distal ends, and a piston having a longitudinal axis and opposing proximal and distal axial ends. Initially, a partially formed piston body is molded. The piston is then completely molded. The distal end of the piston shaft is engaged with the proximal axial end of the piston. The piston engaged with the piston shaft is received in the open proximal end of the barrel.

14 Claims, 2 Drawing Sheets

(56) References Cited

U.S. PATENT DOCUMENTS

| | | | |
|---|---|---|---|
| 2006/0178643 | A1 | 8/2006 | Sudo et al. |
| 2013/0012888 | A1 | 1/2013 | Okihara |

FOREIGN PATENT DOCUMENTS

| | | | |
|---|---|---|---|
| EP | 2981314 | B1 | 7/2019 |
| EP | 3268078 | B1 | 11/2020 |
| JP | 2001029466 | A | 2/2001 |
| JP | 2001190667 | A | 7/2001 |
| JP | 2018023467 | A | 2/2018 |
| WO | 2004044464 | A1 | 5/2004 |
| WO | 2004104553 | A2 | 12/2004 |
| WO | 2009128265 | A1 | 10/2009 |
| WO | 2011059823 | A1 | 5/2011 |

OTHER PUBLICATIONS

Written Opinion issued Oct. 5, 2015 in Int'l Application No. PCT/US2013/035381.

Int'l Preliminary Report on Patentability issued Oct. 15, 2015 in Int'l Application No. PCT/US2013/035381.

PHARMACEUTICAL SYRINGE PISTON

CROSS-REFERENCE TO RELATED APPLICATIONS

This application is a divisional of U.S. patent application Ser. No. 17/828,046, filed May 31, 2022, which is a divisional of U.S. patent application Ser. No. 16/354,675, filed Mar. 15, 2019, and issues as U.S. Pat. No. 11,369,742 on Jun. 28, 2022, which is a continuation of U.S. patent application Ser. No. 14/758,042, filed Jun. 26, 2015, and issued as U.S. Pat. No. 10,258,744 on Apr. 16, 2019, which is a Section 371 of International Patent App. No. PCT/US2013/035381, filed Apr. 5, 2013, which was published in the English language on Oct. 9, 2014 under International Patent Publication No. WO 2014/163645, the disclosures of which are incorporated herein by reference.

BACKGROUND OF THE INVENTION

Embodiments of the present invention relate generally to a pharmaceutical syringe piston, and more particularly, to a pharmaceutical syringe piston with an improved inert film attachment.

U.S. Pat. No. 7,547,297 discloses a rubber syringe piston partially enclosed by an inert film in a cap-like manner. Specifically, the inert film is placed on an outer surface of a tapered face of the piston which faces the contents of a syringe. The inert film prevents contamination of the medicament by materials leaching out of the stopper, and similarly prevents the medicament from penetrating the stopper during extended storage periods, preserving the longevity of the stopper.

However, the film in U.S. Pat. No. 7,547,297 also extends along a cylindrically-shaped portion of the piston. Applicant has discovered that, as a result of this configuration, the inert film abuts against an interior wall of the syringe barrel. This arrangement can increase the breakloose and extrusion (BLE) forces between the stopper and syringe barrel. Higher BLE forces can result in slippage or other errors during injection as the user applies greater pressure to the stopper in order to expel the medicament. In addition, the film contact with the syringe barrel reduces the ability of the rubber material of the stopper to create a seal. The desired seal is at its highest quality when the rubber directly contacts the inner surface of the syringe barrel.

It is desirable to provide a syringe piston that produces low BLE forces with the inner surface of the syringe, and which creates an acceptable seal with the inner surface of the syringe, while still utilizing an inert film to prevent cross-contamination of the syringe piston material with the medicament.

BRIEF SUMMARY OF THE INVENTION

Briefly stated, a preferred embodiment of the present invention comprises a pharmaceutical syringe piston having a longitudinal axis and includes a body having a central face portion oriented essentially perpendicularly with respect to the longitudinal axis of the piston. The central face portion has a first outer circumference and a maximum first diameter measured perpendicularly to the longitudinal axis of the piston. A cylindrical sealing portion proximate the central face portion and oriented coaxially with respect to the longitudinal axis of the piston has a first axial end, a second axial end, and a wall extending therebetween. The wall has a second outer circumference and a second diameter measured perpendicularly to the longitudinal axis of the piston. The second diameter is essentially constant along the longitudinal axis between the first and second axial ends of the cylindrical sealing portion and is larger than the maximum first diameter of the central face portion. An annular curved portion, which connects the first axial end of the cylindrical sealing portion to the first outer circumference of the central face portion, has a maximum outer diameter less than the second diameter of the cylindrical sealing portion. An inert film encloses the central face portion and at least a part of the annular curved portion and has an outer boundary disposed between the first axial end of the cylindrical sealing portion and the first outer circumference of the central face portion.

Another embodiment of the present invention comprises a pharmaceutical syringe for dispensing medicament includes a barrel configured to retain the medicament. The barrel has a longitudinal axis, an inner wall coaxial with respect to the longitudinal axis, a first axial opening, and an opposing second axial opening. A piston body has opposing first and second axial ends and is slidably disposed within the barrel. The piston body has a face portion at a first axial end thereof facing the first axial opening of the barrel. At least a portion of the face portion is enclosed by an inert film having a first outer circumference. The piston body has a sealing portion proximate the face portion. The scaling portion is cylindrically shaped and has a second outer circumference of a size sufficient to maintain the sealing portion in contact with the inner wall of the barrel. The scaling portion also has an outer diameter that is essentially constant along the longitudinal axis of the barrel. The sealing portion is in contact with the inner wall of the barrel at the second outer circumference of the sealing portion. The first outer circumference is smaller than the second outer circumference such that the inert film does not extend axially along any part of the sealing portion.

Still another embodiment of the present invention comprises A pharmaceutical syringe piston having a longitudinal axis and includes a body having a face portion oriented essentially perpendicularly with respect to the longitudinal axis of the piston, and a cylindrical sealing portion having a first axial end proximate the face portion, a second axial end, a wall extending therebetween, and that is oriented coaxially with respect to the longitudinal axis of the piston. The wall has a first outer circumference and a first diameter measured perpendicularly to the longitudinal axis of the piston and that is essentially constant along the longitudinal axis between the first and second axial ends of the cylindrical sealing portion. An inert film enclosies at least a portion of the face portion of the body such that all of an outer surface of the inert film exposed on the piston body lies transverse to the longitudinal axis.

BRIEF DESCRIPTION OF THE SEVERAL VIEWS OF THE DRAWINGS

The foregoing summary, as well as the following detailed description of a preferred embodiment of the invention, will be better understood when read in conjunction with the appended drawings. For the purpose of illustrating the invention, there are shown in the drawings an embodiment which is presently preferred. It should be understood, however, that the invention is not limited to the precise arrangements and instrumentalities shown.

In the drawings.

DETAILED DESCRIPTION OF THE INVENTION

Figure 1:
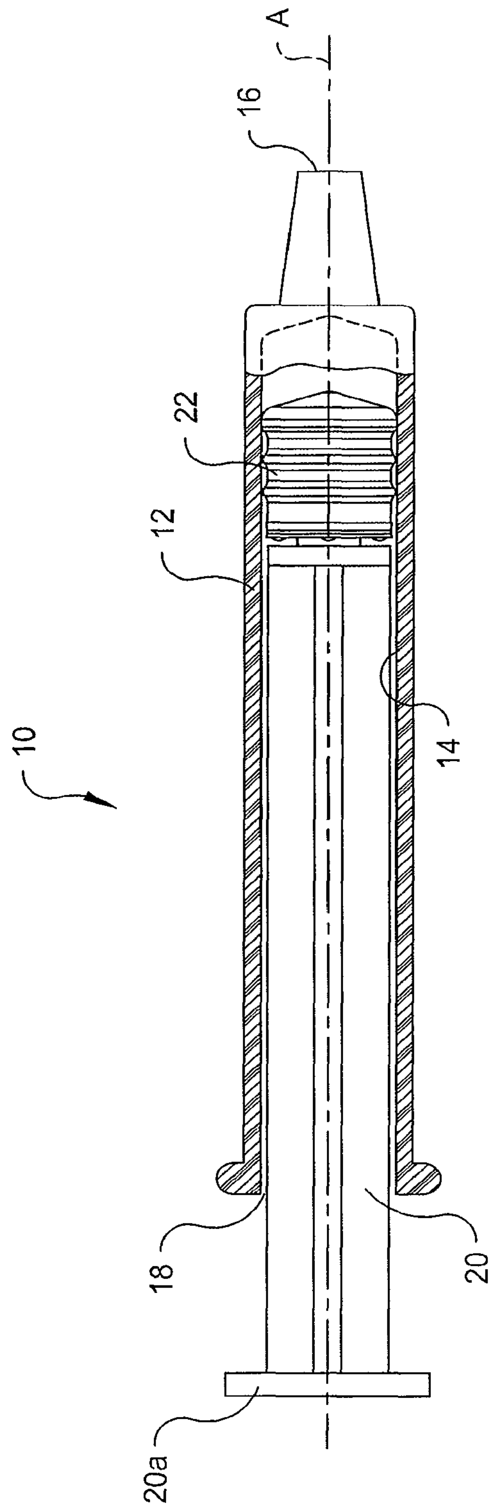
FIG. 1 is a partially sectioned side view of a pharmaceutical syringe containing a piston body in accordance with a preferred embodiment of the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the piston and designated parts thereof. Unless specifically set forth herein, the terms "a", "an" and "the" are not limited to one element but instead should be read as meaning "at least one". The terminology includes the words noted above, derivatives thereof and words of similar import.

Referring to the drawings, wherein the same reference numerals are used to designate the same components throughout the several figures, there is shown in FIG. 1 a pharmaceutical syringe 10 for dispensing medicament (not shown) to a patient. The syringe 10 includes a preferably cylindrically-shaped hollow barrel 12 configured to retain the medicament. The barrel 12 may be made from glass, plastic, or the like, as is conventionally known. The barrel 12 preferably has a longitudinal axis A, and an inner wall 14 that is coaxially disposed about the longitudinal axis A.

The barrel 12 also includes a first axial opening 16 and an opposing second axial opening 18. The first axial opening 16 may be fitted to a delivery device (not shown), such as a conventional needle, transfer device, or the like (not shown), for transporting the medicament from the barrel 12 to the patient. The second axial opening 18 is provided for the receipt and movement of a longitudinally extending plunger shaft 20. The plunger shaft 20 extends from a first axial end (not shown), through the second axial opening 18 of the barrel 12, to a second axial end 20*a*. The first axial end of the plunger shaft 20 engages a piston body 22 slidably disposed within the barrel 12. The piston body 22 is formed substantially of a resilient material, such as rubber or similar elastomer.

Figure 2:
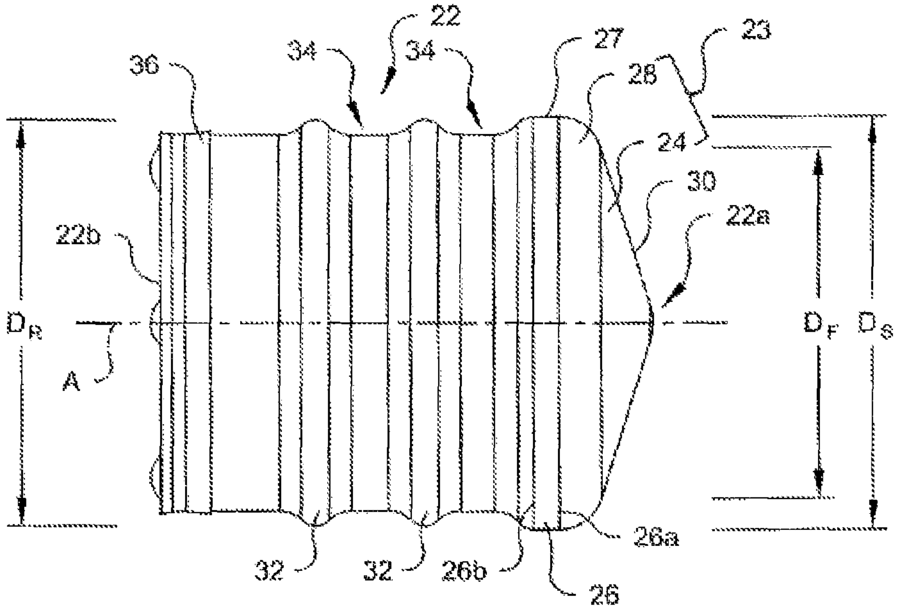
FIG. 2 is a side elevational view of the piston body of FIG. 1.
Figure 3:
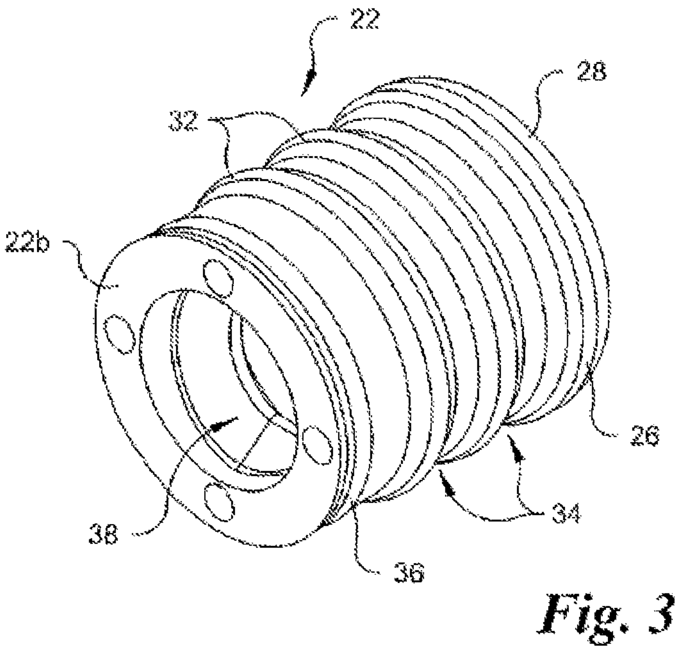
FIG. 3 is a bottom side perspective view of the piston body of FIG. 1.

Referring to FIGS. 2 and 3, the piston body 22 includes opposing first and second axial ends 22*a*, 22*b* and is coaxially disposed with respect to the longitudinal axis A of the barrel 12. The piston body 22 includes a face portion 23 at the first axial end 22*a* thereof that is preferably formed of a central face portion 24 and an annular curved portion 28. The central face portion 24 is preferably oriented essentially perpendicularly with respect to the longitudinal axis A and faces the first axial opening 16 of the barrel 12. In this manner, the central face portion 24 is used to contact the medicament and force it through the first axial opening 16 of the barrel 12. The central face portion 24 also preferably has a maximum diameter DF measured perpendicularly to the longitudinal axis A that defines an outer circumference of the central face portion 24. The central face portion 24 preferably has a conical shape, such that a center thereof is spaced apart from the outer circumference thereof along the longitudinal axis A. However, the shape of the central face portion 24 is not so limited, and may also be frusto-conical, flat, rounded, or the like. The inner wall 14 of the barrel 12 proximate the first axial opening 16 may be shaped to complement the shape of the central face portion 24 of the piston body 22.

The piston body 22 further includes a sealing portion 26 proximate the face portion 23 which, when the piston body 22 is disposed within the barrel 12, is in contact with the inner wall 14 of the barrel 12. The sealing portion 26 preferably has a first axial end 26*a*, a second axial end 26*b*, and a wall 27 extending therebetween, which is preferably cylindrically shaped and lies along the longitudinal axis A of the syringe 10 when the piston body 22 is disposed in the barrel 14. The cylindrically shaped part of the scaling portion 26 preferably has a diameter $D_S$, measured perpendicularly to the longitudinal axis A, that is essentially constant along the longitudinal axis A between the first and second axial ends 26*a*, 26*b* of the sealing portion 26, and which defines an outer circumference thereof to contact the inner wall 14 of the barrel 12. This contact provides a fluid-tight seal to prevent medicament from seeping past the piston body 22 and toward the second axial opening 18. It is preferred that the maximum diameter DF of the central face portion 24 is smaller than the diameter $D_S$ of the sealing portion 26.

The maximum outer circumference of the central face portions 24 of the piston body 22 may be connected to the first axial end 26*a* of the sealing portion 26 by the annular curved portion 28 of the face portion 23. Preferably, the curved portion 28 is outwardly convex in shape, as shown in FIG. 2, such that the radius of curvature extends into the piston body 22. However, other configurations may be used to connect the outer circumferences of the central face and sealing portions 24, 26, such as concave shapes (e.g., wherein the radius of curvature extends away from the piston body 22), multiple convex/concave curves, or the like. The annular curved portion 28 preferably has an outer diameter that is smaller than the diameter DS of the scaling portion 26.

In preferred embodiments of the present invention, the central face portion 24 and at least a portion of the annular curved portion 28 of the piston body 22 are enclosed by an inert film 30. The film 30 is preferably made from a fluorinated polymer material, as is generally known. To avoid the disadvantages described above, the film 30 preferably does not extend axially beyond the first axial end 26*a* of the sealing portion 26 or along any part of the sealing section 26. That is, the film 30 is disposed coaxially with the longitudinal axis and has an outer circumference that is smaller in size than the outer circumference of the sealing portion 26, which is sufficiently sized to maintain contact of the sealing portion 26 of the piston body 22 with the inner wall 14 of the barrel 12. Preferably, the outer boundary of the film 30 is disposed between the first axial end 26*a* of the cylindrical sealing portion 26 and the outer circumference of the central face portion 24. As a result of this configuration, the outer surface of the inert film 30 that lies exposed on the piston body 22 is transverse to the longitudinal axis A. In this way, contact with the inner wall 14 by the inert film 30 is minimized while the critical function of maintaining a contamination seal between the piston body 22 and the drug in contact therewith.

It is preferred that the piston body 22 also include at least one, and more preferably a plurality, of radially protruding stabilizing ribs 32 that are disposed between the sealing portion 26 and the second axial end 22*b* of the piston body 22. Each rib 32 includes a diameter $D_R$ measured perpendicularly to the longitudinal axis A and an outer circumference, each of which may be identical for each rib 32, as shown in FIGS. 1-3. However, the circumference and diameter $D_R$ may differ between ribs 32, as desired. It is preferred that the outer circumference and diameter $D_R$ of the ribs 32 are smaller than the respective outer circumference and diameter $D_S$ of the sealing portion 26 such that the ribs 32 have minimal contact with the inner wall 14 of the barrel 12. The ribs 32 are provided primarily for stabilizing the piston body 22 within the syringe 10, although the ribs 32 may perform some sealing functions within the barrel 12, and it is desired to avoid adding unnecessary forces between the piston body 22 and the barrel 12.

The ribs 32 are preferably spaced apart along the longitudinal axis A from each other, and from the sealing portion 26 of the piston body 22, by one or more annular recesses 34, which are disposed between adjacent ribs 32 and between the second axial end 26*b* of the sealing portion 26 and an adjacent rib 32. The diameter and circumference of the piston body 22 at each annular recess 34 may vary as necessary, as the material of the piston body 22 within each recess 34 generally will not have much interaction with the overall syringe 10.

Toward the second axial end 22*b* of the piston body 22 will be a trim edge 36, which is where the completed piston body 22 is separated from a sheet (not shown) containing a plurality of piston bodies 22 manufactured together as will be described in further detail below. The outer circumference and diameter of the trim edge are preferably smaller than the corresponding dimensions of the ribs 32 so as to have no interaction with the inner wall 14 of the barrel 12. In addition, the trim edge 36 does not need to be disposed as shown in FIGS. 1-3, but may instead be placed elsewhere on the piston body 22. Moreover, the trim edge 36 may form one of the other components of the piston body 22, such as a rib 32, annular recess 34, the sealing portion 26, or the like.

A receiving cavity 38 is formed from the second axial end 22*b* of the piston body 22 and extends longitudinally within the piston body 22. The receiving cavity 38 is configured to receive the first axial end of the plunger shaft 20. The receiving cavity 38 may be sized and dimensioned as appropriate to securely receive the plunger shaft 20, which is preferably attached to the piston body 22 via a screw thread (not shown), although other connection types, such as friction or interference fits, adhesives, welding, mechanical fasteners, and the like may be used.

It is also preferred that at least a portion of the piston body 22 is coated with a lubricant to further lower BLE forces between the piston body 22 and the inner wall 14 of the barrel 12. The lubricant further prevents the piston body 22 from sticking to the inner wall 14 during the injection process.

A process for manufacturing the piston body 22 will now be described. First, a non-vulcanized rubber sheet (not shown) together with a foil-like inert film (not shown) may be placed between die plates of a forming tool (not shown). The inert film, which is initially flat, can be firmly joined with the rubber sheet. However, the film and rubber sheet may be introduced between the die plates independently from one another and placed loosely on top of each other. The rubber sheet is vulcanized under the influence of heat and pressure and is non-detachably joined with the inert film. The forming tool forms the face portion 23, including the central face portion 24 and annular curved portion 28, as well as the sealing portion 26 of the piston body 22 in this first step.

The partially formed piston bodies 22 may thereafter be blanked out from the rubber sheet and placed into a second forming tool (not shown). A second non-vulcanized rubber sheet (not shown) is also placed into the second forming tool. Under the influence of heat and pressure, the second rubber sheet is vulcanized and molded to form the remainder of the piston body 22 to the second axial end 22*b*, all of which is joined to the sealing portion 26 at the second axial end 26*b* thereof. During this process, the receiving cavity 38 is also molded into the piston body 22 from the second axial end 22*b*. Subsequently, the piston body 22 is blanked out from the rubber sheet at the trim edge 36.

Although this is the preferred method for manufacturing the piston body 22 in accordance with the present invention, other methods for the formation of a piston body 22 and the attachment of an inert film to the piston body 22 may be used.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

What is claimed is:

1. A method for manufacturing a syringe, the syringe having a longitudinal axis and comprising a barrel, a piston shaft, and a piston the method comprising:
- vulcanizing at least a portion of a first rubber sheet and at least a portion of an inert film between die plates of a first forming tool;
- forming, with the first forming tool, a first portion of the piston out of the portion out of the first rubber sheet that is vulcanized to the portion of the inert film, the first portion of the piston comprising a central face portion and an annular curved portion, the central face portion and at least a part of the annular curved portion being enclosed by the portion of the inert film;
- blanking out the first portion of the piston together with the portion of the inert film from the first rubber sheet and the inert film;
- vulcanizing a portion of a second rubber sheet and the first portion of the piston together, the portion of the second rubber sheet vulcanized to the first portion of the piston being a second portion of the piston;
- blanking out the second portion of the piston from the second rubber sheet to form a trim edge of the second portion of the piston, which is spaced apart from the portion of the inert film on the first portion of the piston;
- engaging the piston shaft with the piston; and
- receiving the piston engaged with the piston shaft within the barrel, wherein an entirety of the portion of the inert film that is blanked out extends transverse to the longitudinal axis of the syringe.

2. The method of claim 1, wherein the first portion of the piston further comprises a sealing portion proximately connected to the annular curved portion, the sealing portion having an outer circumference that contacts an inner wall of the barrel.

3. The method of claim 2, wherein the inert film terminates distal to the sealing portion.

4. The method of claim 2, wherein the piston has at least one stabilizing rib proximal to the sealing portion.

5. The method of claim 4, wherein the sealing portion and the at least one stabilizing rib each have an outer diameter measured perpendicularly to the longitudinal axis of the piston, the outer diameter of the sealing portion being greater than the outer diameter of the at least one stabilizing rib.

6. The method of claim 5, wherein the trim edge has an outer diameter measured perpendicularly to the longitudinal axis of the piston, the outer diameter of the at least one stabilizing rib being greater than the outer diameter of the trim edge.

7. The method of claim 4, wherein the trim edge is proximally spaced apart from the at least one stabilizing rib.

8. The method of claim 2, wherein the trim edge is proximally spaced apart from the sealing portion.

9. The method of claim 1, wherein the central face portion is flat or convex.

10. The method of claim 1, further comprising forming a receiving cavity extending distally from a proximal axial end of the piston.

11. The method of claim 1, wherein the inert film is made of a fluorinated polymer material.

12. The method of claim 2, wherein the inert film has an outer circumference smaller than the outer circumference of the sealing portion.

13. The method of claim 2, wherein the inert film has an outer boundary disposed between a distal end of the sealing portion and an outer circumference of the central face portion.

14. The method of claim 4, wherein the at least one stabilizing rib has a plurality of stabilizing ribs.

* * * * *